US011957720B2

(12) United States Patent
McLean et al.

(10) Patent No.: US 11,957,720 B2
(45) Date of Patent: *Apr. 16, 2024

(54) BIFIDOBACTERIUM LONGUM AND FUNCTIONAL GI DISORDERS

(71) Applicant: SOCIÉTÉ DES PRODUITS NESTLÉ S.A., Vevey (CH)

(72) Inventors: Peter McLean, Lausanne (CH); Gabriela Bergonzelli Degonda, Bussigny (CH); Stephen Michael Collins, Ontario (CA); Premysl Bercik, Ontario (CA); Elena Verdu de Bercik, Ontario (CA)

(73) Assignee: Societe des Produits Nestle S.A., Vevey (CH)

( * ) Notice: Subject to any disclaimer, the term of this patent is extended or adjusted under 35 U.S.C. 154(b) by 20 days.

This patent is subject to a terminal disclaimer.

(21) Appl. No.: 17/730,891

(22) Filed: Apr. 27, 2022

(65) Prior Publication Data
US 2022/0280576 A1    Sep. 8, 2022

Related U.S. Application Data

(63) Continuation of application No. 16/023,503, filed on Jun. 29, 2018, now Pat. No. 11,452,745, which is a (Continued)

(30) Foreign Application Priority Data

Aug. 25, 2009 (EP) .................................... 09168590

(51) Int. Cl.
*A61K 35/745* (2015.01)
*A23K 10/18* (2016.01)
(Continued)

(52) U.S. Cl.
CPC .............. *A61K 35/74* (2013.01); *A23K 10/18* (2016.05); *A23L 33/135* (2016.08);
(Continued)

(58) Field of Classification Search
CPC .... A61K 35/74; A61K 35/745; A61K 35/744; A23L 33/135; A23K 10/18; A23Y 2300/55; A23Y 2300/00
See application file for complete search history.

(56) References Cited

U.S. PATENT DOCUMENTS

| 4,332,790 A | 6/1982 | Sozzi et al. |
| 6,887,850 B2 | 5/2005 | Fuchs et al. |

(Continued)

FOREIGN PATENT DOCUMENTS

| DE | 10008279 | 8/2001 |
| EP | 1961308 | 8/2008 |

(Continued)

OTHER PUBLICATIONS

Salminen S et al., "Probiotics: How Should They Be Defined?," Trends Food Sci. Technol., vol. 10 (1999), pp. 107-110.
(Continued)

*Primary Examiner* — Allison M Fox
*Assistant Examiner* — Qing Xu
(74) *Attorney, Agent, or Firm* — K&L Gates LLP

(57) ABSTRACT

The present invention generally relates to the field of probiotic bacteria. In particular, it relates to methods for treating or preventing functional GI disorders comprising administering *Bifidobacterium longum*, such as *Bifidobacterium longum* ATCC BAA-999.

15 Claims, 3 Drawing Sheets

Related U.S. Application Data continuation of application No. 13/391,343, filed as application No. PCT/EP2010/062320 on Aug. 24, 2010, now Pat. No. 10,028,981.

(51) Int. Cl.
  *A23L 33/135*  (2016.01)
  *A61K 35/74*  (2015.01)
  *C12N 1/20*  (2006.01)
  *A23K 20/163*  (2016.01)
  *A23L 33/21*  (2016.01)

(52) U.S. Cl.
  CPC .............. *A61K 35/745* (2013.01); *C12N 1/20* (2013.01); *A23K 20/163* (2016.05); *A23L 33/21* (2016.08); *A23V 2002/00* (2013.01); *A23V 2400/533* (2023.08)

(56) References Cited

U.S. PATENT DOCUMENTS

| | | | |
|---|---|---|---|
| 7,033,629 B2 | 4/2006 | Koss | |
| 8,343,482 B2* | 1/2013 | Bergonzelli | A23L 33/135 424/93.3 |
| 2006/0093592 A1 | 5/2006 | Cheruvanky et al. | |
| 2006/0204485 A1 | 9/2006 | Dinan et al. | |
| 2007/0128178 A1 | 6/2007 | Corthesy-Theulaz et al. | |
| 2008/0145341 A1 | 6/2008 | Myatt et al. | |
| 2009/0192226 A1 | 7/2009 | Neu | |
| 2009/0269307 A1 | 10/2009 | Albers | |
| 2011/0182869 A1 | 7/2011 | Knol et al. | |
| 2020/0289587 A1* | 9/2020 | Kiely | A23L 33/135 |

FOREIGN PATENT DOCUMENTS

| | | |
|---|---|---|
| EP | 1974735 | 10/2008 |
| EP | 2110028 | 10/2009 |
| FR | 2443247 | 7/1980 |
| WO | 0042168 | 7/2000 |
| WO | 2004069156 | 8/2004 |
| WO | 2004071520 | 8/2004 |
| WO | 2004112507 | 12/2004 |
| WO | 2007093619 | 8/2007 |
| WO | 2007101675 | 9/2007 |
| WO | 2008116708 | 10/2008 |
| WO | 2008116904 | 10/2008 |
| WO | 2010008272 | 1/2010 |

OTHER PUBLICATIONS

Longstreth et al., "Functional bowel disorders," Gastroenterology, vol. 35, No. 3, (2006), pp. 91-105.
Puccio et al, "Clinical evaluation of a new starter formula for infants containing live Bifidobacterium longum BL999 and prebiotics," Nutrition, vol. 23, No. 1, Dec. 22, 2006, pp. 1-8, XP005812913.
McFarland LV et al, "Meta-analysis of probiotics for the treatment of irritable bowel syndrome," World Journal of Gastroenterology, May 7, 2008, vol. 14, No. 17, pp. 2650-2661.
Hoveyda N et al., "A systematic review and meta-analysis: probiotics in the treatment of irritable bowel syndrome," BMC Gastroenterology, (2009), vol. 9, No. 15, pp. 1-11.
PCT International Search Report for Application No. PCT/EP2010/062320 dated Sep. 27, 2010. 4 Pages.
Drouault-Holowacz et al. "A double blind randomized controlled trial of a probiotic combination in 100 patients with irritable bowel syndrome" Gastroenterologie Clinique et Biologique, 2008, vol. 32, pp. 147-152, XP002521958.
Cappello et al. "A randomised clinical trial (RCT) of a symbiotic mixture in patients with irritable bowel syndrome (IBS): effects on symptoms, colonic transit and quality of life" Int. J. Colorectal Dis., 2013, vol. 28, pp. 349-358.
Shimizu et al. "Immuno-modulating effects of Bifidobacterium longum BB536" Medical Science Digest, 2006, vol. 32, No. 9, pp. 405-408 (cited in Office Action issued in corresponding Japanese Patent Application No. P2015-219799 dated Sep. 20, 2016).
Article in Digestion & Absorption at vol. 29, No. 1, 2006, pp. 107-114 (cited in Office Action issued in corresponding Japanese Patent Application No. P2015-219799 dated Sep. 20, 2016).
Article in the Food Industry at vol. 44, No. 4, 2001, pp. 34-39 (cited in Office Action issued in corresponding Japanese Patent Application No. P2015-219799 dated Sep. 20, 2016).
Office Action issued in corresponding Japanese Patent Application No. P2015-219799 dated Sep. 20, 2016 and English translation of same.
European Office Action—Application No. 10 74 7 451 .2-1403 dated Mar. 23, 2017—2 pages.
Hyman et al., "Childhood Functional Gastrointestinal Disorders: Neonate/Toddler," Gastroenterology (2006), vol. 130, pp. 1519-1526—XP005451630.
Wikipedia—Irritable bowel syndrome, downloaded from the website https://en.wikipedia.org/wiki/irritable_bowel_syndrome on Mar. 11, 2017.
Wikipedia printout, Lactic acid bacteria.
Corinaldesi et al., Alimentary Pharmacology & Therapeuties, 30:245-252, published online on May 12, 2009.
Clemente, Trends in Food Science & Technology, 11:254-262, 2000.
Abe et al., International Journal of Food Science & Technology, 44(4):718-724, published in Apr. 2009.
Bell et al., Derwent abstract of U.S. Pat. No. 5,968,896 (Year: 1998).
Wikipedia printout—whey protein, downloaded on Sep. 16, 2021 from https://en.wikipedia.org/wiki/Whey_protein (Year: 2021).
Logan et al., "Major depressive disorder: probiotics may be an adjuvant therapy", Medical Hypotheses, 2005, vol. 64, pp. 533-538.
Xiao et al., "Effect of yogurt containing Bifidobacterium long um BB 536 on the defecation frequency and fecal characteristics of healthy adults : A double-blind crossover study", Japanese Journal of Lactic Acid Bacteria, 2007, vol. 18, No. 1, pp. 31-36.
Diop et aL, "Probiotic Food Supplement Reduces Stress-Induced Gastrointestinal Symptoms in Volunteers: A Double-Blind, Placebo-Controlled, Randomized Trial", Nutrition Research, vol. 28, Issue No. 1, 2008, pp. 1-5.
Gruenwald et aL, "Effect of a Probiotic Multivitamin Compound on Stress and Exhaustion", Advances in Natural Therapy, vol. 19, Issue No. 3, 2002, pp. 141-150.
Faniguulo et al., "Role of Gut Microflora and Problotic Effects in the Irritable Bowel Syndrome", Acta Biomed, vol. 77, Issue No. 2, 2006, pp. 85-89.
Printout of Irritable bowel syndrome, downloaded on Mar. 13, 2020 from Mayo Clinic website: https://www.mayoclinic.org/diseases-conditions/irritable-bowel-syndrome/symptoms-causes/syc-20360016 (Year: 2020).

* cited by examiner

BIFIDOBACTERIUM LONGUM AND FUNCTIONAL GI DISORDERS

CROSS REFERENCE TO RELATED APPLICATIONS

The present application is a continuation of U.S. patent application Ser. No. 16/023,503 filed Jun. 29, 2018, which is a continuation of U.S. patent application Ser. No. 13/391,343 filed May 15, 2012, now U.S. Pat. No. 10,028,981 issued Jul. 24, 2018, which is a National Stage of International Application No. PCT/EP2010/062320 filed Aug. 24, 2010, which claims priority to European Patent Application No. 09168590.9 filed Aug. 25, 2009, the entire contents of each of which are incorporated herein by reference.

FIELD OF THE INVENTION

The present invention generally relates to the field of probiotic bacteria. In particular it relates to *Bifidobacterium longum* NCC3001 (ATCC BAA-999) subsequently referred to as *Bifidobacterium longum* ATCC BAA-999, and its use in ingestible compositions. The composition described in the present invention may be used to treat or prevent functional gastro-intestinal (GI) disorders.

BACKGROUND

Functional GI disorders (FGIDs) are a group of disorders including Irritable bowel syndrome (IBS) and Functional dyspepsia that are chronic conditions associated with high morbidity characterized by abdominal discomfort or pain, bloating and in the case of IBS altered bowel habits (diarrhoea and/or constipation).

The prevalence of FGIDs in the general population is relatively high ranging from 15%-30% having a substantial economic burden. It has been suggested that the annual direct costs for IBS alone are now around $US41 billion in the 8 most industrialised countries with considerable additional indirect costs (e.g., absenteeism from work etc.). Current treatments for FGIDs demonstrate at best marginal efficacy which has been historically related to poor understanding of the disease pathogenesis.

The precise pathophysiology of IBS remains to be elucidated.

Recent studies have described mucosal inflammation and alterations in intestinal microflora in IBS patients and a disease correlation with intestinal infections.

The fact that some probiotics exhibit anti-bacterial, antiviral and anti-inflammatory properties and that they can restore the intestinal microbiota balance, suggested that they may become suitable therapeutic agents for IBS.

To date several studies on the effect of different probiotics on IBS subjects have been published. These studies suggest that probiotic use may be associated with improvement in IBS symptoms but also that not all probiotics have equal efficacy in IBS.

Several meta-analysises performed recently concluded that there is inadequate data to comment on the efficacy of other probiotics (Lynne V McFarland, et al., World J Gastroenterol 2008 May 7; 14(17): 2650-2661; Nourieh Hoveyda, et al., BMC Gastroenterology 2009, 9: 15).

Consequently, it was the object of the present invention to improve the state of the art and in particular to provide the art with a composition comprising an alternative bacterial strain that is effective, readily available, low priced and safe to administer without unwanted side effects which can be used to treat or prevent functional GI disorders.

The present inventors have addressed this need. They were surprised to see that they could achieve this object by the subject matter of the independent claims. The dependent claims further develop the idea of the present invention.

DETAILED DESCRIPTION

Figure 1:
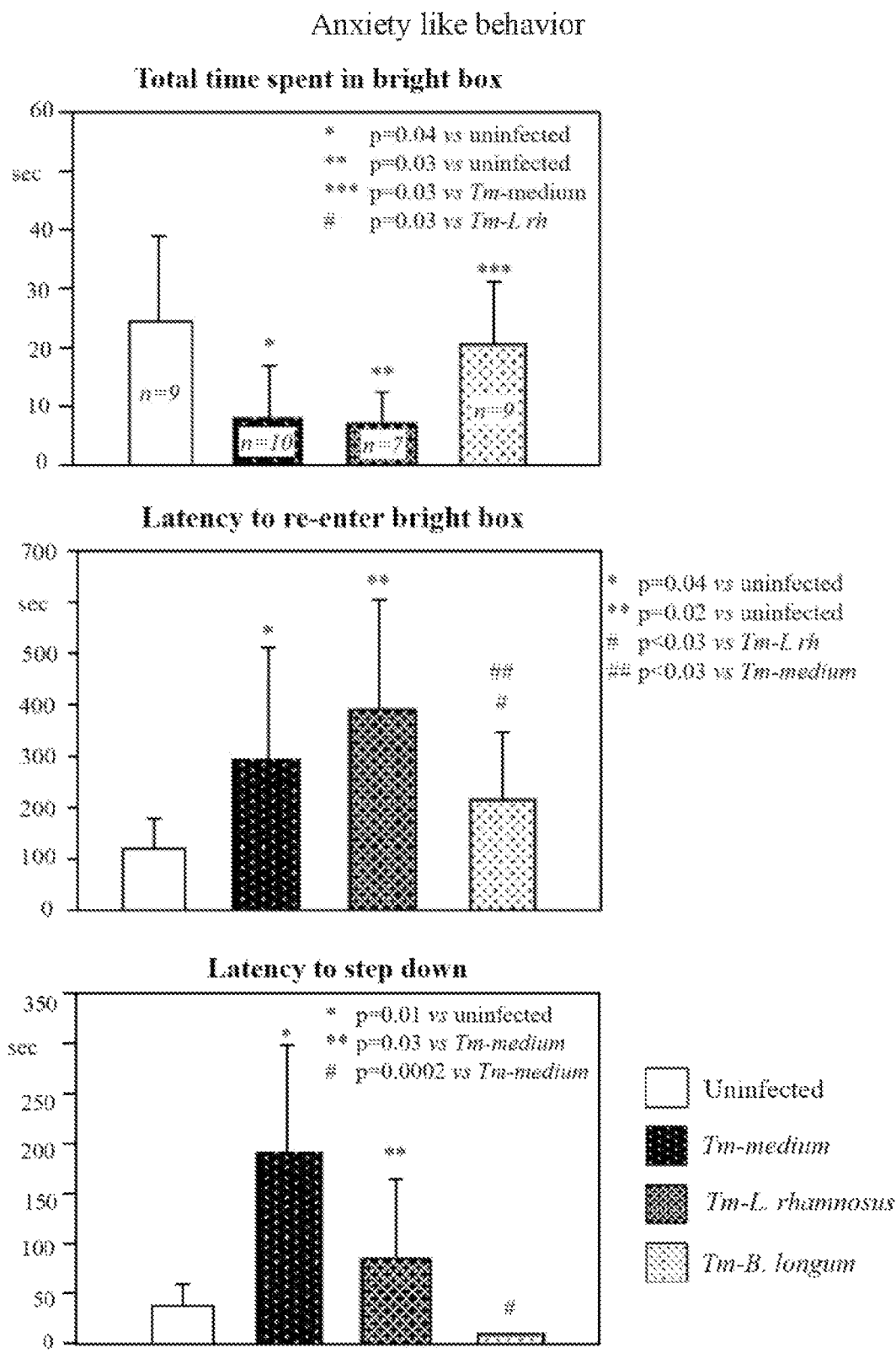
FIG. 1 shows the result of a dark box/bright box test.

It was found that the effectiveness in treating and/or preventing functional GI disorders depends on the bacterial genus, species and strain used.

Consequently, one embodiment of the present invention is a composition comprising *Bifidobacterium longum* ATCC BAA-999, and/or its fermented growth medium for use in the treatment and/or prevention of functional GI disorders.

The present invention also relates to the use of *Bifidobacterium longum* ATCC BAA-999 for the preparation of a composition to treat and/or prevent functional GI disorders.

[0015] *Bifidobacterium longum* ATCC BAA-999 was one strain of the species *Bifidobacterium longum* that was found to be in particular effective in achieving the object of the present invention.

Advantageously, *Bifidobacterium longum* ATCC BAA-999 is commercially available and was already tested and found to be acceptable for addition to food products, for example.

*Bifidobacterium longum* ATCC BAA-999 (BL999) may be obtained commercially from specialist suppliers, for example from Morinaga Milk Industry Co. Ltd. of Japan under the trade mark BB536.

*Bifidobacterium longum* ATCC BAA-999 (BL999) may be cultured according to any suitable method. It may be added to products in a freeze-dried or spray-dried form, for example.

The term "*Bifidobacterium longum* ATCC BAA-999 (BL999)" is meant to include the bacterium, parts of the bacterium and/or a growth medium fermented by the bacterium.

The composition may be any composition, but is preferably a composition to be administered orally, enterally or rectally.

For example, the composition may be an edible composition.

"Edible" means a material that is approved for human or animal consumption.

Typically, the composition may be selected from the group consisting of a food composition, a pet food composition, a dietary supplement, a nutraceutical, a nutritional formula, a drink, and/or a medical composition.

If the composition of the present invention is a food composition, this has the advantage that such a composition can be distributed in pharmacies, drug stores, but also in normal supermarkets, where the compositions are easily available to everybody.

The generally pleasant taste of food compositions will further contribute to the acceptance of the product. In particular small children or pets are much more likely to readily consume compositions with a taste that is generally liked.

Examples of food products that are applicable to the present invention are yoghurts, milk, flavoured milk, ice cream, ready to eat desserts, powders for re-constitution with, e.g., milk or water, chocolate milk drinks, malt drinks, ready-to-eat dishes, instant dishes or drinks for humans or food compositions representing a complete or a partial diet intended for pets or livestock.

Consequently, in one embodiment the composition according to the present invention is a food product intended for humans, pets or livestock.

The composition may be intended for animals selected from the group consisting of dogs, cats, pigs, cattle, horses, goats, sheep or poultry.

In a preferred embodiment, the composition is a food product intended for adult species, in particular human adults.

The composition of the present invention may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials. The composition may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like. In all cases, such further components will be selected having regard to their suitability for the intended recipient.

The composition may be a nutritionally complete formula.

The composition according to the invention may comprise a source of protein.

Any suitable dietary protein may be used, for example animal proteins (such as milk proteins, meat proteins and egg proteins); vegetable proteins (such as soy protein, wheat protein, rice protein, and pea protein); mixtures of free amino acids; or combinations thereof. Milk proteins such as casein and whey, and soy proteins are particularly preferred.

The proteins may be intact or hydrolysed or a mixture of intact and hydrolysed proteins. It may be desirable to supply partially hydrolysed proteins (degree of hydrolysis between 2 and 20%), for example for human subjects and/or animals at risk of developing cows' milk allergy.

Furthermore, pre-hydrolysed protein sources are generally easier digested and absorbed by an impaired gastrointestinal tract.

If hydrolysed proteins are required, the hydrolysis process may be carried out as desired and as is known in the art. It may be desirable to supply partially hydrolysed proteins (degree of hydrolysis between 2 and 20%).

For example, a whey protein hydrolysate may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

The composition may also contain a source of carbohydrates and a source of fat.

If the composition includes a fat source, the fat source preferably provides 5% to 40% of the energy of the composition; for example 20% to 30% of the energy. A suitable fat profile may be obtained using a blend of canola oil, corn oil and high-oleic acid sunflower oil.

A source of carbohydrate may be added to the composition.

The source of carbohydrates preferably provides 40% to 80% of the energy of the composition. Any suitable carbohydrate may be used, for example sucrose, lactose, glucose, fructose, corn syrup solids, maltodextrins, and mixtures thereof. Dietary fibre may also be added if desired. Dietary fibre passes through the small intestine undigested by enzymes and functions as a natural bulking agent and laxative. Dietary fibre may be soluble or insoluble and in general a blend of the two types is preferred. Suitable sources of dietary fibre include soy, pea, oat, pectin, guar gum, partially hydrolysed guar gum, gum Arabic, fructooligosaccharides, acidic oligosaccharides, galacto-oligosaccharides, sialyl-lactose and oligosaccharides derived from animal milks. A preferred fibre blend is a mixture of inulin with shorter chain fructo-oligosaccharides. Preferably, if fibre is present, the fibre content is between 2 and 40 g/l of the composition as consumed, more preferably between 4 and 10 g/l.

The composition may also contain minerals and micronutrients such as trace elements and vitamins in accordance with the recommendations of Government bodies such as the USRDA. For example, the composition may contain per daily dose one or more of the following micronutrients in the ranges given:—300 to 500 mg calcium, 50 to 100 mg magnesium, 150 to 250 mg phosphorus, 5 to 20 mg iron, 1 to 7 mg zinc, 0.1 to 0.3 mg copper, 50 to 200 µg iodine, 5 to 15 µg selenium, 1000 to 3000 µg beta carotene, 10 to 80 mg Vitamin C, 1 to 2 mg Vitamin B1, 0.5 to 1.5 mg Vitamin B6, 0.5 to 2 mg Vitamin B2, 5 to 18 mg niacin, 0.5 to 2.0 µg Vitamin B12, 100 to 800 µg folic acid, 30 to 70 µg biotin, 1 to 5 µg Vitamin D, 3 to 10 µg Vitamin E.

One or more food grade emulsifiers may be incorporated into the composition if desired; for example diacetyl tartaric acid esters of mono- and di-glycerides, lecithin and mono- and di-glycerides. Similarly suitable salts and stabilisers may be included.

The composition may be orally and/or enterally administrable; for example in the form of a powder for re-constitution with milk or water.

According to one preferred embodiment of the present invention the composition comprises at least one other kind of other food grade micro-organism.

"Food grade" micro-organisms are micro-organisms that are safe for use in food.

The food grade micro-organisms are preferably food-grade bacteria or food-grade yeast. The food grade bacteria may be selected from the group consisting of lactic acid bacteria, bifidobacteria, propionibacteria or mixtures thereof. As food grade yeast for example *Saccharomyces cerevisiae* and/or *Saccharomyces boulardii* can be used.

The food grade bacteria may be probiotic bacteria.

"Probiotic" means microbial cell preparations or components of microbial cells with a beneficial effect on the health or well-being of the host. (Salminen S, Ouwehand A Benno Y. et al "Probiotics: how should they be defined" Trends Food Sci. Technol. 1999:10 107-10).

Probiotic bacteria are preferably selected from the group consisting of lactic acid bacteria, bifidobacteria, propionibacteria or mixtures thereof. Probiotic bacteria may be any lactic acid bacteria or bifidobacteria with established probiotic characteristics. For example they may be also capable of promoting the development of a bifidogenic intestinal microbiota.

Suitable probiotics may be selected from the group consisting of *Bifidobacterium, Lactobacillus, Streptococcus* and *Saccharomyces* or mixtures thereof, in particular selected from the group consisting of *Bifidobacterium longum, Bifidobacterium lactis, Lactobacillus acidophilus, Lactobacillus rhamnosus, Lactobacillus paracasei, Lactobacillus johnsonii, Lactobacillus plantarum, Lactobacillus salivarius, Enterococcus faecium, Saccharomyces boulardii* and *Lactobacillus reuteri* or mixtures thereof, preferably selected from the group consisting of *Lactobacillus johnsonii* (NCC533; CNCM I-1225), *Bifidobacterium longum* (NCC490; CNCM I-2170), *Bifidobacterium longum* (NCC2705; CNCM I-2618), *Bifidobacterium lactis* (2818; CNCM I-3446), *Lactobacillus paracasei* (NCC2461; CNCM I-2116), *Lactobacillus rhamnosus* GG (ATCC53103), *Lactobacillus rhamnosus* (NCC4007; CGMCC 1.3724), *Enterococcus faecium* SF 68 (NCIMB10415), and mixtures thereof.

In a preferred embodiment of the present invention the composition further contains at least one prebiotic. "Prebiotic" means food substances intended to promote the growth of probiotic bacteria in the intestines.

Prebiotics can thus promote the growth of certain food grade bacteria, in particular of probiotic bacteria, in the intestines and can hence enhance the effect of *Bifidobacterium longum* ATCC BAA-999. Furthermore, several prebiotics have a positive influence on, e.g., digestion.

Preferably the prebiotic may be selected from the group consisting of oligosaccharides and optionally contain fructose, galactose, mannose, soy and/or inulin; dietary fibers; or mixtures thereof.

The *Bifidobacterium longum* ATCC BAA-999, may be used, both, as living bacterium as well as inactivated non-replicating bacterial species.

"Non-replicating" means that no viable cells and/or colony forming units can be detected by classical plating methods. Such classical plating methods are summarized in the microbiology book: James Monroe Jay, Martin J. Loessner, David A Golden. 2005. Modern food microbiology. 7th edition, Springer Science, New York, N.Y. 790 p. Typically, the absence of viable cells can be shown as follows: no visible colony on agar plates or no turbidity in liquid growth medium after inoculation with different concentrations of bacterial preparations ('non replicating' samples) and incubation under appropriate conditions (aerobic and/or anaerobic atmosphere for at least 24 h).

It is preferred that at least a part of the *Bifidobacterium longum* ATCC BAA-999, are alive in the composition and preferably arrive alive in the intestine. This way they can persist in the intestine and may increase their effectiveness by multiplication. They may also be effective by interacting with the commensal bacteria and/or the host.

For special sterile food products or medicaments, for example, it might be preferable that *Bifidobacterium longum* ATCC BAA-999 is present in a non-replicating form in the composition. Hence, in one embodiment of the present invention at least a part of the *Bifidobacterium longum* ATCC BAA-999, are non-replicating in the composition.

In therapeutic applications, compositions are administered in an amount sufficient to at least partially cure or arrest the symptoms of the disease and its complications. An amount adequate to accomplish this is defined as "a therapeutically effective dose". Amounts effective for this purpose will depend on a number of factors known to those of skill in the art such as the severity of the disease and the weight and general state of the patient.

In prophylactic applications, compositions according to the invention are administered to a patient susceptible to or otherwise at risk of a particular disease in an amount that is sufficient to at least partially reduce the risk of developing a disease. Such an amount is defined to be "a prophylactic effective dose". Again, the precise amounts depend on a number of patient specific factors such as the patient's state of health and weight.

Generally, *Bifidobacterium longum* ATCC BAA-999 will be administered in a therapeutically effective dose and/or in a prophylactic effective dose.

If *Bifidobacterium longum* ATCC BAA-999 is present in a viable form, it is theoretically effective in any concentration considering the fact that these bacteria can colonize the gut and multiply.

For the composition of the present invention it is generally preferred that a daily dose of the composition comprises between $10^4$ and $10^{12}$ cfu (colony forming units) of *Bifidobacterium longum* ATCC BAA-999. A particular suitable daily dose of *Bifidobacterium longum* ATCC BAA-999, is from $10^4$ to $10^{11}$ cfu, more preferably from $10^4$ to $10^{10}$ cfu.

The composition of the present invention may also comprise between $10^2$ and $10^{10}$ cfu, preferably $10^2$ to $10^9$ colony forming units, more preferably from $10^2$ to $10^8$ cfu of *Bifidobacterium longum* ATCC BAA-999, per gram dry weight of the composition.

In the case of inactivated and/or non-replicating *Bifidobacterium longum* ATCC BAA-999, it is generally preferred that the composition of the present invention comprises between $10^2$ and $10^{10}$ non-replicating cells of *Bifidobacterium longum* ATCC BAA-999, per gram of the dry weight of the composition. A particular suitable dose of *Bifidobacterium longum* ATCC BAA-999, is from $10^3$ to $10^8$ non-replicating cells, more preferably from $10^5$ to $10^8$ non-replicating cells per gram of the dry weight of the composition.

Obviously, non-replicating micro-organisms do not form colonies, consequently, the term cells is to be understood as the amount of non replicating micro-organisms that is obtained from the specified amount of replicating bacterial cells. This includes micro-organisms that are inactivated, non viable or dead or present as fragments such as DNA or cell wall materials.

The composition of the present invention may be provided in powder form having a water activity smaller than 0.2, for example in the range of 0.19-0.05, preferably smaller than 0.15.

The composition may be a shelf stable powder. The low water activity provides this shelf stability and ensures that probiotic micro-organism, e.g., *Bifidobacterium longum* ATCC BAA-999, will remain viable even after long storage times. Water activity or aw is a measurement of the energy status of the water in a system It is defined as the vapor pressure of water divided by that of pure water at the same temperature; therefore, pure distilled water has a water activity of exactly one.

Additionally or alternatively, the probiotic micro-organism *Bifidobacterium longum* ATCC BAA-999 may be provided in an encapsulated form It has been found that encapsulation of the bacteria has therapeutical and technical advantages. Encapsulation increases the survival of the bacteria and thus the number of live bacteria which arrive in the intestine. Furthermore, the bacteria are gradually released allowing a prolonged action of the bacteria on the health of the subject. Bacteria may be micro-encapsulated, for example as described by FR2443247 (Societe des Produits Nestle), incorporated herein by reference. Briefly, the bacteria may be freeze or spray dried and incorporated into a gel.

The present inventors were in particular surprised to find that the composition of the present invention can successfully be used to significantly increase hippocampal BDNF expression.

BDNF (Brain-derived neurotrophic factor) is a growth factor from a unique family of polypeptide growth factors. BDNF and other neurotrophic factors, e.g., NGF (nerve growth factor), NT-3 (neurotrophin-3), and NT-4 (neurotrophin-4) are essential for the health and well-being of the nervous system This effect might possibly explain the observed effect against functional bowel disorders.

The term "functional GI disorder" refers to a group of bowel disorders which are characterised by chronic abdominal complaints without a structural or biochemical cause that could explain symptoms.

Functional GI disorders are well known to those of skill in the art and are for example described and defined as functional gastrointestinal disorders with symptoms attributable to the middle or lower gastrointestinal tract by Longstreth et al., in GASTROENTEROLOGY 2006; 130: 1480-1491, for example.

The functional GI disorder may be selected from the group consisting of irritable bowel syndrome; functional dyspepsia; functional constipation, functional diarrhoea; functional abdominal pain; functional bloating, Epigastric Pain Syndrome, Postprandial Distress Syndrome or combinations thereof.

Functional GI disorders that may be treated or prevented by the subject matter of the present invention comprise anxiety linked functional GI disorders, for example.

Anxiety is a psychological and physiological state which results in an unpleasant feeling that is typically associated with uneasiness, fear, or worry. Anxiety is for example a normal reaction to stress. It may help a person to deal with a difficult situation at work or at school, but—when excessive—anxiety disorders result, one group of which are anxiety linked functional GI disorders.

The inventors—without wishing to be bound by theory—presently believe that the underlying mechanism by which the compositions of the present invention are effective is related to the modulation of the bidirectional microbial-gut-brain axis, possibly significantly associated with psychological factors.

It is clear to those skilled in the art that any features described in this specification can be combined freely without departing from the scope of the present invention as disclosed. In particular, all features described for the composition of the present invention are applicable to the use of the present invention and vice versa.

Further features and advantages of the present invention result from the following Examples and Figures:

FIG. 1 shows the result of a dark box/bright box test: total time spent in bright box, latency to re-enter bright box and latency to step down in mice infected with *Trichuris muris* (Tm). Tm-medium and Tm-*B. longum* are Tm infected mice treated with fresh medium (negative control) and *Bifidobacterium longum* ATCC BAA-999, respectively; a Tm group treated with *L. rhamnosus* (L. rh) strain is shown for comparison.

Figure 2:
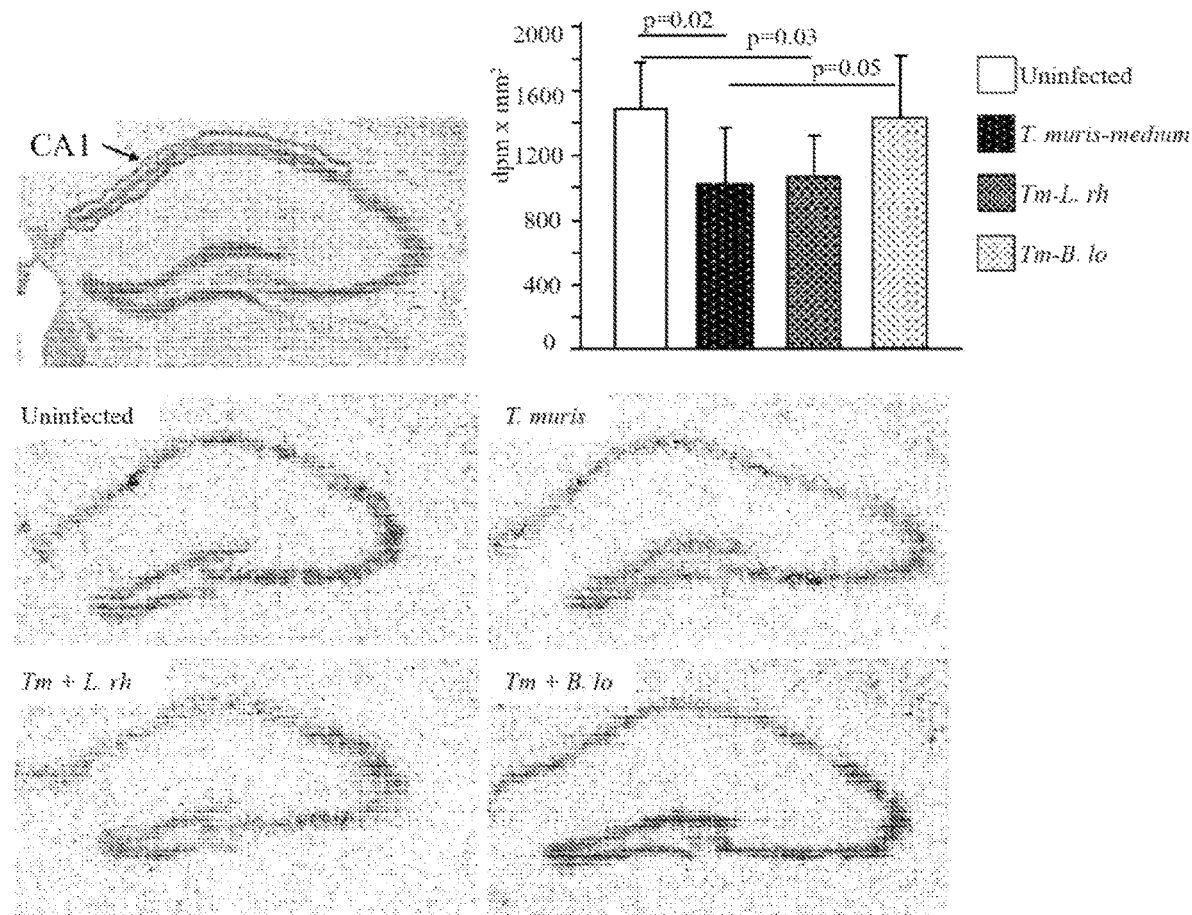
FIG. 2 shows the results of an in situ hybridization in the brain hippocampal region of mice infected with *Trichuris muris* (Tm).

FIG. 2 shows the results of the in situ hybridization in the brain hippocampal region of mice infected with a *Trichuris muris* (Tm). Tm-*B. longum* is Tm infected mice treated with *Bifidobacterium longum* ATCC BAA-999; a Tm group of mice treated with *L. rhamnosus* strain is shown for comparison. Quantification of 35S signals was performed by autoradiography and image analysis (right upper panel).

Figure 3:
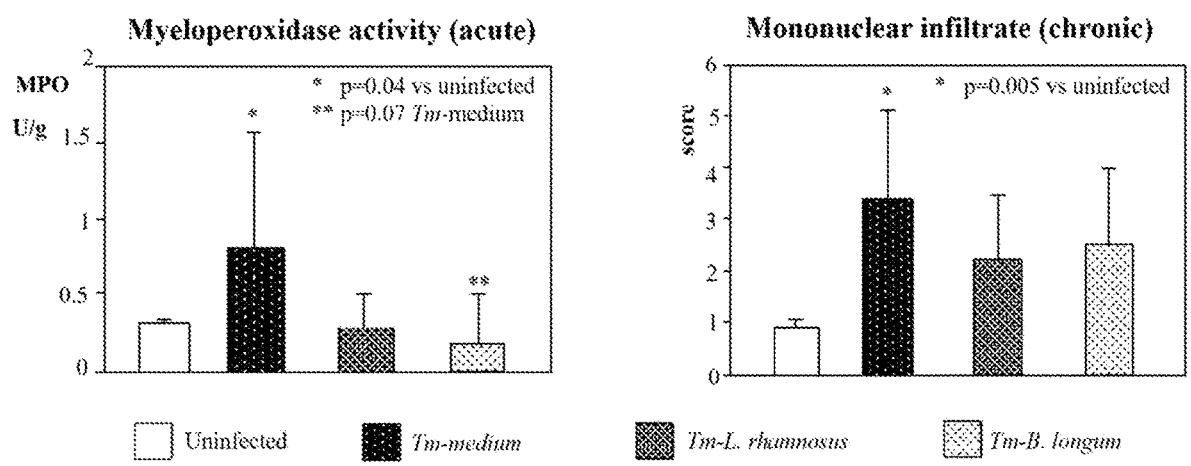
FIG. 3 shows the results obtained on colonic inflammation measured by myeloperoxidase activity assay (left panel) and mononuclear cell infiltration (right panel) in mice infected with *Trichuris muris* (Tm).

FIG. 3 shows the results obtained on colonic inflammation measured by myeloperoxidase activity assay (left panel) and mononuclear cell infiltration (right panel) in mice infected with *Trichuris muris* (Tm). Tm-medium and Tm-*B. longum* are Tm infected mice treated with fresh medium (negative control) and *Bifidobacterium longum* ATCC BAA-999; a Tm group of mice treated with *L. rhamnosus* strain is shown for comparison.

Examples

Material and Methods
Bacterial Culture Conditions:

Probiotics (*Bifidobacterium longum* ATCC BAA-999 and *L. rhamnosus* NCC4007 for comparison) were grown under anaerobic conditions in Man-Rogosa-Sharpe (MRS, BioMerieux) broth (bifidobacteria with 0.5% cysteine). After 24 h at 37° C., the number of bacteria was estimated by measuring the optical density at 600 nm (1 OD600=$10^8$ bacteria/mL). Bacterial cells were pelleted by centrifugation at 5000×g for 15 min at 4° C. and further resuspended at a concentration of $10^{10}$/mL in their spent culture medium Aliquots of 1 mL were kept frozen until use.

Animals:

Male BALB/c or AKR mice (Harlan, Canada) were purchases at the age of 6-8 wks and housed in a conventional specific pathogen free Unit at McMaster University Central Animal Facility. All experiments were conducted with approval from the McMaster University Animal Care Committee.

Design:
Chronic *T muris* Infection:

Male AKR mice were gavaged with *T. muris* (300 eggs/mouse) (n=26) or with placebo (n=9). Infected mice were then gavaged daily with *L. rhamnosus, B. longum* or fresh MRS from day 30 for 10 days. Uninfected mice were gavaged with fresh MRS on a daily basis from day 30 to day 40. At the end of probiotic or placebo administration, the mice underwent dark box/bright box and step-down tests. The mice were sacrificed thereafter and tissue samples were obtained. Colon samples were fixed in formalin for histological analysis or were snap frozen for MPO determination. Brains were snap frozen in liquid nitrogen and stored for in situ hybridization.

Behavior Testing:
Dark Box/Bright Box:

Anxiety behavior was assessed individually in mice using dark box/bright box as described in the literature. Briefly, each mouse was placed in the center of illuminated bright box (30×30 cm) connected by an opening (10×3 cm) to smaller dark box (30×15 cm). The locomotor behavior of each mouse in the bright box was recorded for 10 min by a digital video camera and stored in a computer for an off-line analysis. Several parameters were assessed by a blinded observer including total time spent in bright box, latency to re-enter bright box (time spent in dark box after first entry), and number of crossovers (number of crossing from dark box to bright box).

Step-down test: Anxiety behavior was assessed using step down test as described in the literature. Briefly, each mouse was placed in the center of an elevated platform (7.5 cm in diameter, 3 cm high) positioned in the middle of a black floor. Latency to step down from the pedestal was measured by a stop-watch; maximum duration of the test was 5 min.

Histology:

Colon Samples were Fixed University

10% formalin and then stained with hematoxylin-eosin. The slides were examined under light microscopy to grade for acute and chronic inflammatory infiltrate.

Myeloperoxidase Activity Assay:

In order to assess acute intestinal inflammation, myeloperoxidase activity (MPO) assay was performed on frozen tissues as described previously. MPO activity is expressed in units per mg of tissue, where one unit of MPO is defined as a quantity of the enzyme able to convert 1 μmol of hydrogen peroxide to water in 1 minute at room temperature.

In Situ Hybridization in the CNS:

Levels of BDNF in hippocampus and CRH in hypothalamus (paraventricular nucleus) were assessed by in situ hybridizations using 35S-labeled RNA probes on frozen brain sections as described previously (Whitfield et al., 1990; Foster et al., 2002). Briefly, brains were removed and rapidly frozen by immersion in 2-methylbutane at −60° C., and stored at −70° C. Cryostat-cut 12-μm-thick coronal sections were thaw-mounted onto gelatine-coated slides, dried, and stored at −35° C. Tissue sections were fixed with 4% formaldehyde, acetylated with 0.25% acetic anhydride in 0.1 M triethanolamine-HCl, pH 8.0, dehydrated, and delipidated with chloroform. Antisense BDNF ribonucleotide probe (gift of Dr. J. Lauterborn and Dr. C. Gall, University of California Irvine) and anti-sense CRH ribonucleotide probe (gift of Dr. James Herman, University of Cincinnati) was transcribed from linearized plasmid using the Riboprobe System (Promega Biotech, Burlington, ON) with a-35S-UTP (specific activity >1000 Ci/mmol; Perkin-Elmer, Boston, MA) and T3 and T7 polymerases respectively. Radiolabelled probes were diluted in a hybridization buffer (0.6 M NaCl, 10 mM Tris pH 8.0, 1 mM EDTA pH 8.0, 10% Dextran sulfate, 0.01% sheared salmon sperm DNA, 0.05% total yeast RNA, type XI, 0.01% yeast tRNA, IX Denhardt's solution) and applied to brain sections (approximately 500,000 CPM/section). Slides were incubated overnight at 55° C. in a humidified chamber. To reduce nonspecific binding of the probe, slides were washed in 20 μg/ml RNase solution for 30 min at room temperature, followed by 1 h each in 2×SSC at 50° C., 0.2×SSC at 55° and 60° C. Slides were dehydrated and air-dried for autoradiography. Slides and 14C plastic standards were placed in x ray cassettes, apposed to film (BioMax MR; Eastman Kodak, Rochester, NY) for 5 days and developed (Kodak Medical X-Ray Processor). Autoradiographic film images of brain sections and standards were digitized with a solid-state camera with a 60 mm Nikon lens using QCapture software (Qicam; Quorum Technologies Inc., Guelph, ON) and a Macintosh computer-based image analysis system with Image software. Light transmittance through the film was measured by outlining the structure on the monitor. For BDNF mRNA, transmittance was converted to radioactivity levels using the Rodbard curve applied to the standards. For CRH mRNA, the density slice feature was utilized to measure both the light transmittance and the area of mRNA signal. The calculated DPM were then multiplied by area to produce a measurement of integrated density. Illustrations were made directly from the captured images.

Statistical Analysis:

Data are presented as mean±standard deviation or medians with interquartile ranges as appropriate. Data was analysed using either two-way ANOVA, test or non-paired t-test as appropriate. A p value of <0.05 was considered as statistically significant.

Results:

Mice chronically infected with the parasite *Trichuris muris* showed an increase in anxiety-like behaviour in two behavioural tests: 1) In the dark box/bright box test, infected animals showed a decrease in the time spent in the bright box and an increase of the latency to re-enter the bright box; 2) In the step down test, the infection increased the latency to step down from the pedestal (FIG. 1). Treatment with *Bifidobacterium longum* ATCC BAA-999 but not with *L. rhamnosus* NCC4007 induced a reduction of anxiety-like behaviour towards normality. The effect on behaviour was correlated with a normalization of *Trichuris muris*-mediated decrease in BDNF levels in the hippocampus by *B. longum* only (FIG. 2). In contrast, treatment with *B. longum* as well as with *L. rhamnosus* resulted in a reduction of myeloperoxidase activity and mononuclear infiltration previously induced by *Trichuris muris* infection (FIG. 3) indicating that the normalization of behaviour was independent of the anti-inflammatory effect of the bacteria.

The invention claimed is:

1. A method for treatment of irritable bowel syndrome and anxiety in a subject in need thereof, the method comprising:
   administering to the subject a composition comprising *Bifidobacterium longum* ATCC BAA-999 and a B vitamin,
   wherein the composition is selected from the group consisting of a dietary supplement, a nutraceutical, a drink, and a medical composition.

2. The method of claim 1, wherein the composition comprises at least one other type of food grade bacteria.

3. The method of claim 2, wherein the at least one other type of food grade bacteria is selected from the group consisting of lactic acid bacteria and propionibacteria.

4. The method of claim 1, wherein the composition comprises at least one prebiotic.

5. The method of claim 4, wherein the at least one prebiotic is selected from the group consisting of oligosaccharides and dietary fibers.

6. The method of claim 1, wherein at least 5% of *Bifidobacterium longum* ATCC BAA-999 cells are viable in the composition.

7. The method of claim 1, wherein at least 80% of *Bifidobacterium longum* ATCC BAA-999 cells are non-replicating in the composition.

8. The method of claim 1, wherein the composition comprises between $10^4$ and $10^{10}$ cells of *Bifidobacterium longum* ATCC BAA-999 per daily dose.

9. The method of claim 1, wherein the composition comprises between $10^2$ and $10^8$ cells of *Bifidobacterium longum* ATCC BAA-999 per g dry weight of the composition.

10. The method of claim 1, wherein the composition comprises a protein source comprising hydrolyzed whey protein.

11. The method of claim 1, wherein the composition is in powder form having a water activity of less than 0.2.

12. The method of claim 1, wherein the B vitamin is selected from the group consisting of Vitamin B1, Vitamin B6, Vitamin B2, niacin, Vitamin B12, folic acid, biotin, and mixtures thereof.

13. The method of claim 1, wherein the composition comprises at least one of 1 to 2 mg Vitamin B1, 0.5 to 1.5 mg Vitamin B6, 0.5 to 2 mg Vitamin B2, 5 to 18 mg niacin, 0.5 to 2.0 μg Vitamin B12, 100 to 800 μg folic acid, or 30 to 70 μg biotin.

14. The method of claim 1, wherein the composition further comprises at least one of a protein, a fat source, and a source of carbohydrates.

15. The method of claim 14, wherein the composition further comprises at least one of 5 wt. % to 40 wt. % of a fat source and 40 wt. % to 80 wt. % of a source of carbohydrates.

* * * * *